US00PP23162P2

(12) United States Plant Patent
Suiker

(10) Patent No.: US PP23,162 P2
(45) Date of Patent: Nov. 6, 2012

(54) STRAWBERRY PLANT NAMED 'FLAIR'

(50) Latin Name: *Fargaria L.*
Varietal Denomination: Flair

(75) Inventor: Marcellus Emanuel Suiker, Vollenhove (NL)

(73) Assignee: El Santa Beheer B.V., Ens (NL)

( * ) Notice: Subject to any disclaimer, the term of this patent is extended or adjusted under 35 U.S.C. 154(b) by 0 days.

(21) Appl. No.: 13/134,665

(22) Filed: Jun. 14, 2011

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner* — Kent L Bell

(74) *Attorney, Agent, or Firm* — E. A. Whealy

(57) ABSTRACT

A new and distinct cultivar of Strawberry plant named 'Flair', characterized by its open plant habit and vigorous growth habit; early flowering habit; early and uniform fruit ripening; glossy, medium to firm fruits that are orange red in color; pleasant fruit aroma and taste; and excellent fruit postharvest longevity.

3 Drawing Sheets

Botanical designation: *Fragaria L.*
Cultivar denomination: 'FLAIR'.

BACKGROUND OF THE INVENTION

The present Invention relates to a new and distinct cultivar of Strawberry plant, botanically known as *Fragaria L.* and hereinafter referred to by the name 'Flair'.

The new Strawberry plant is a product of a planned breeding program conducted by the Inventor in Ens, The Netherlands. The objective of the breeding program was to develop new early-ripening Strawberry plants with an open plant density, good fruit quality, ease of harvesting and good postharvest longevity.

The new Strawberry plant originated from a cross-pollination made by the Inventor in April, 2003 of a proprietary Strawberry selection identified as code name Flevo 00-24-7, not patented, as the female, or seed, parent with a proprietary Strawberry selection identified as code name Flevo 00-08-4, not patented, as the male, or pollen, parent. The new Strawberry plant was discovered and selected by the Inventor as a single plant from within the progeny of the stated cross-pollination in a controlled environment in Ens, The Netherlands in June, 2004.

Asexual reproduction of the new Strawberry plant by cuttings in a controlled environment at Ens, The Netherlands since July, 2004, has shown that the unique features of this new Strawberry plant are stable and reproduced true to type in successive generations of asexual reproduction.

SUMMARY OF THE INVENTION

Plants of the new Strawberry have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Flair'. These characteristics in combination distinguish 'Flair' as a new and distinct Strawberry plant:

1. Open plant habit and vigorous growth habit.
2. Early flowering habit.
3. Early and uniform fruit ripening.
4. Glossy, medium to firm fruits that are orange red in color.
5. Pleasant fruit aroma and taste.
6. Excellent fruit postharvest longevity.

Plants of the new Strawberry differ from plants of the female parent selection in the following characteristics:

1. Plants of the new Strawberry are more open than and not as compact as plants of female parent selection.
2. Leaves of plants of the new Strawberry are longer than leaves of plants of the female parent selection.
3. Fruits of plants of the new Strawberry ripen five days earlier than fruits of plants of the female parent selection.

Plants of the new Strawberry differ from plants of the male parent selection in the following characteristics:

1. Plants of the new Strawberry have longer inflorescences than plants of male parent selection.
2. Fruits of plants of the new Strawberry ripen five days earlier than fruits of plants of the male parent selection.
3. Fruits of plants of the new Strawberry do not split readily whereas fruits of plants of the male parent selection tend to split just below the calyx.

Plants of the new Strawberry can be compared to plants of Strawberry 'Honeoye', not patented. In side-by-side comparisons conducted in Ens, The Netherlands, plants of the new Strawberry differed from plants of 'Honeoye' in the following characteristics:

1. Plants of the new Strawberry were more open than and not as compact and dense as plants of 'Honeoye'.
2. Plants of the new Strawberry were more vigorous than plants of 'Honeoye'.
3. Leaves of plants of the new Strawberry were slightly longer than leaves of plants of 'Honeoye'.
4. Plants of the new Strawberry flowered earlier than plants of 'Honeoye'.
5. Fruits of plants of the new Strawberry ripened five days earlier than fruits of plants of 'Honeoye'.
6. Plants of the new Strawberry had a shorter harvesting period than plants of 'Honeoye'.

7. Fruits of plants of the new Strawberry were firmer than fruits of plants of 'Honeoye'.
9. Fruits of plants of the new Strawberry and 'Honeoye' differed in color as fruits of 'Honeoye' were red in color.
10. Fruits of plants of the new Strawberry had better post-harvest longevity than fruits of plants of 'Honeoye'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photographs on the first sheet are side perspective views of typical fruiting plants of 'Flair' grown in raised ground beds.

The photographs on the second sheet are close-up views of typical fruits of 'Flair'.

The photographs on the third sheet are close-up views of typical leaves of 'Flair'.

DETAILED BOTANICAL DESCRIPTION

The aforementioned photographs, following observations and measurements describe plants grown during the spring in raised ground beds in an outdoor nursery in Ens, The Netherlands and under typical Strawberry production practices. During the production of the plants, day temperatures ranged from 8° C. to 30° C. and night temperatures ranged from 0° C. to 20° C. Plants were one year old when the photographs and description were taken. In the following description, color references are made to The Royal Horticultural Society Colour Chart, 2001 Edition, except where general terms of ordinary dictionary significance are used.

Botanical classification: *Fragaria L.* 'Flair'.

Parentage:

*Female, or seed, parent*.—Proprietary seedling selection of *Fragaria L.* identified as code name Flevo 00-24-7, not patented.

*Male, or pollen, parent*.—Proprietary seedling selection of *Fragaria L.* identified as code name Flevo 00-08-4, not patented.

Propagation:

*Type*.—By cuttings.

*Time to produce a rooted young plant*.—About 30 days.

*Root description*.—Medium in thickness, fibrous; light brown in color.

*Rooting habit*.—Moderately branching; medium density.

Plant description:

*Plant form and growth habit*.—Perennial plants that are globose in form; open plant form; leaves basal; vigorous growth habit; rapid growth rate; few crowns develop per plant.

*Plant height*.—About 20 to 25 cm.

*Plant diameter*.—About 40 to 45 cm.

Leaf description:

*Arrangement*.—Basal rosette; compound with typically three leaflets.

*Leaflet length*.—About 9 to 12 cm.

*Leaflet width*.—About 8 to 11 cm.

*Leaflet shape*.—Broadly ovate.

*Leaflet apex*.—Obtuse.

*Leaflet base*.—Attenuate to obtuse.

*Leaflet margin*.—Serrate.

*Leaflet texture, upper and lower surfaces*.—Pubescent.

*Leaflet venation*.—Pinnate.

*Leaflet color*.—Developing leaflets, upper surface: Close to 137A. Developing leaflets, lower surface: Close to 138A. Fully expanded leaflets, upper surface: Close to 137A; venation, close to 137A. Fully expanded leaflets, lower surface: Close to 137C; venation, between 144C and 137C.

*Petioles*.—Length: About 8 to 23 cm. Diameter: About 2.5 to 5 mm. Texture, upper surface: Weak to medium blistering. Texture, lower surface: Smooth. Color, upper surface: Close to 145A to 145B. Color, lower surface: Close to 145A.

Flower description:

*Flower form and flowering habit*.—Rotate flowers arranged singly at lateral apices; flowers held at the foliar plane; flowering not remontant.

*Fragrance*.—None detected.

*Natural flowering season*.—Early flowering habit; plants begin flower mid-April in Ens, The Netherlands.

*Flower diameter*.—About 3 to 4 cm.

*Flower depth* (*height*).—About 5 mm.

*Petals*.—Arrangement: Single whorl of six petals; petals not imbricate. Length: About 1.2 cm. Width: About 1.2 cm. Shape: Broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of eight to twelve sepals; calyx, star-shaped; calyx situated above the fruit; attitude of the calyx segments is spreading and slightly larger than the fruit diameter; adherence of the calyx is weak to moderate. Length: About 1 cm to 1.5 cm. Width: About 5 mm. Shape: Lanceolate. Apex: Acute. Base: Fused. Margin: Entire. Texture, upper and lower surfaces: Pubescent. Color, upper surface: Close to 137A. Color, lower surface: Close to 137C.

*Peduncles*.—Length: About 10 cm to 16 cm. Diameter: About 3 mm to 4 mm. Strength: Strong. Texture: Pubescent. Color: Close to 144B.

*Pedicels*.—Length: About 2.5 cm to 6 cm. Diameter: About 1 mm to 3 mm. Strength: Strong. Texture: Pubescent. Color: Close to 144B.

*Reproductive organs*.—Stamens: Quantity per flower: About 30. Anther length: About 2 mm. Anther color: Close to 14B. Pollen amount: Abundant. Pollen color: Close to 15C. Pistils: Quantity per flower: About 60. Stigma shape: Rounded. Stigma color: Close to 5A. Fruits: Time of ripening: From flowering to fruit development, about 26 days in Ens, The Netherlands. Postharvest longevity: Long, about five to ten days. Length: About 3 cm to 6 cm. Diameter: About 2.5 cm to 5 cm. Shape: Conical to rounded cordate. Hollow center: Absent or very weakly expressed. Firmness: Medium to firm. Fragrance, taste: Pleasant; good balance between sweetness and acidity. Luster: Glossy. Surface unevenness: Absent or very weak. Color: Close to 34A. Flesh color: Close to 33A. Achene insertion: Below the fruit surface. Achene color: Close to 1A; on shoulders of the fruit, close to 34A.

Disease and pest resistance: Plants of the new Strawberry have not been noted to be resistant to pathogens and pests common to Strawberry.

Temperature tolerance: Plants of the new Strawberry have been observed to tolerate temperatures ranging from 0° C. to 35° C.

It is claimed:

1. A new and distinct Strawberry plant named 'Flair' as illustrated and described.

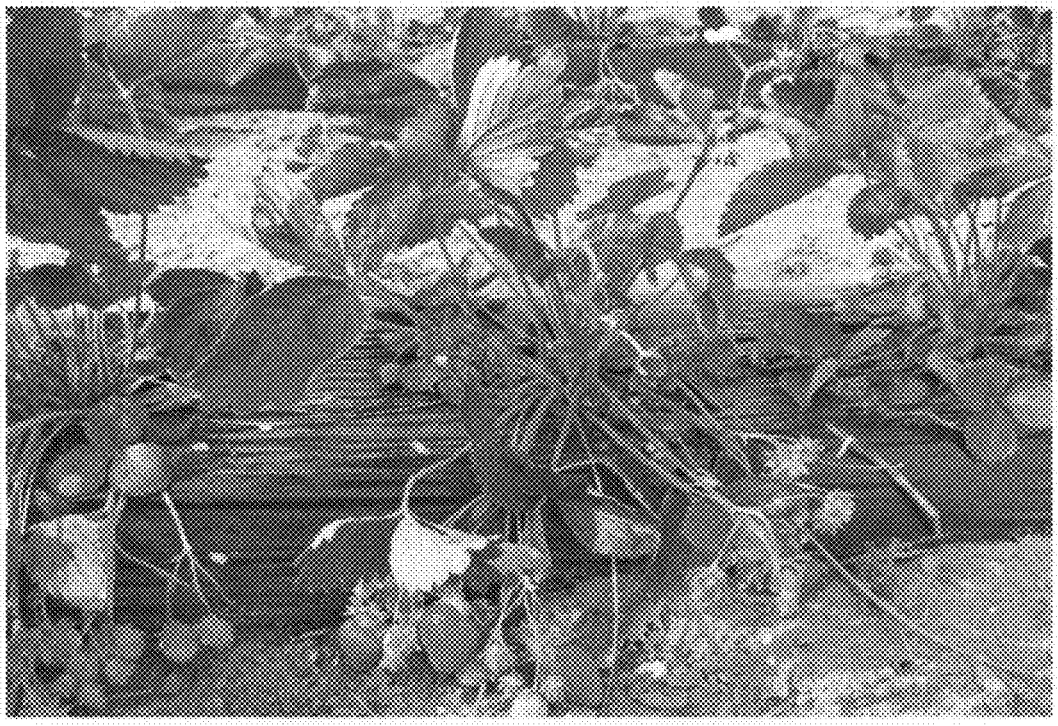
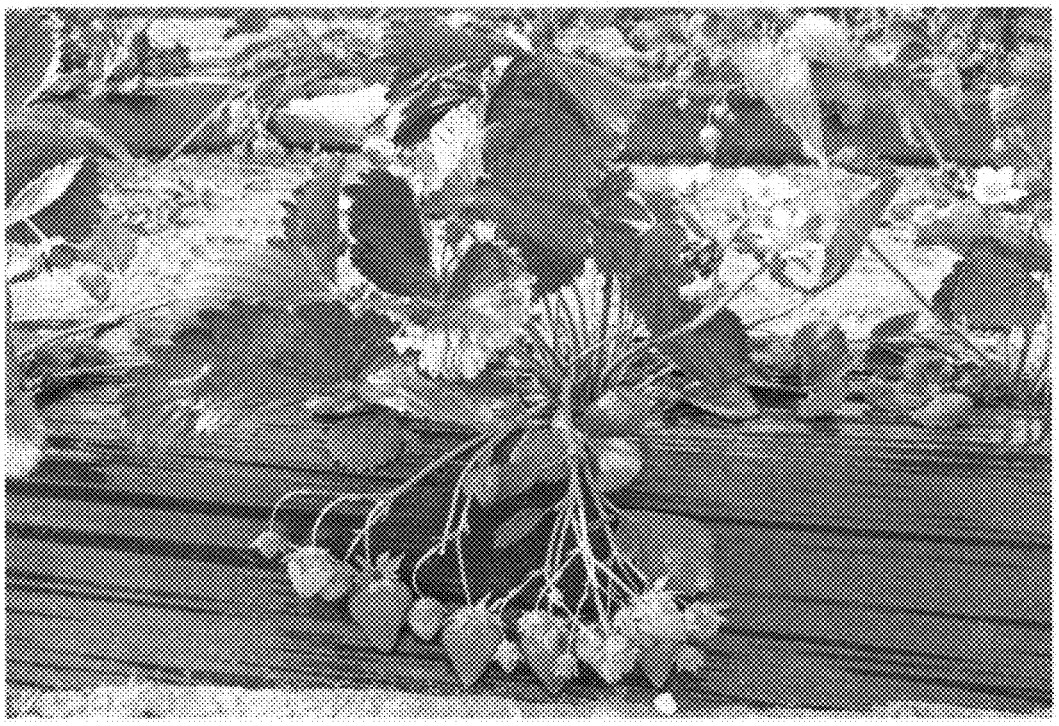

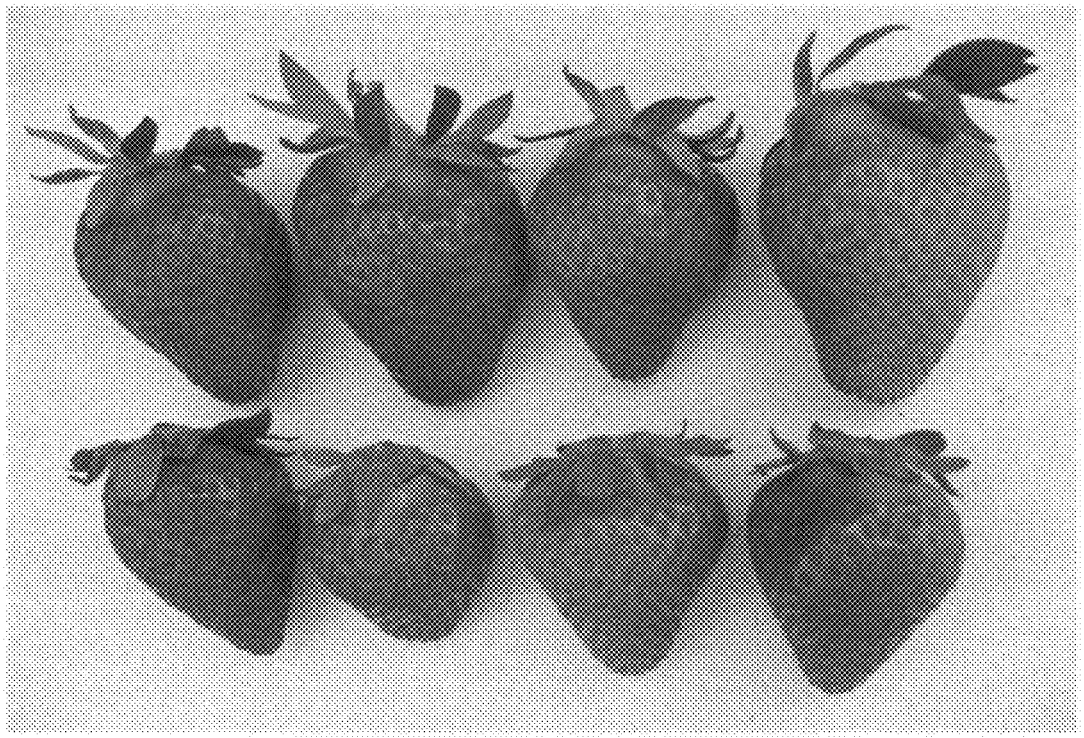
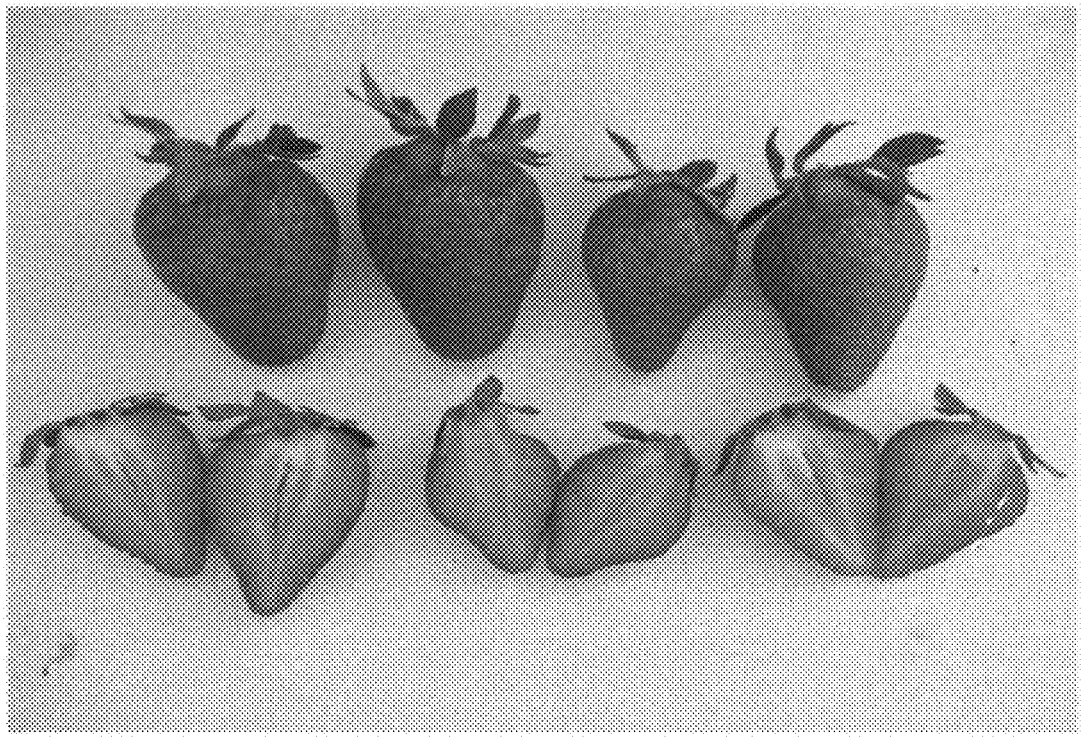

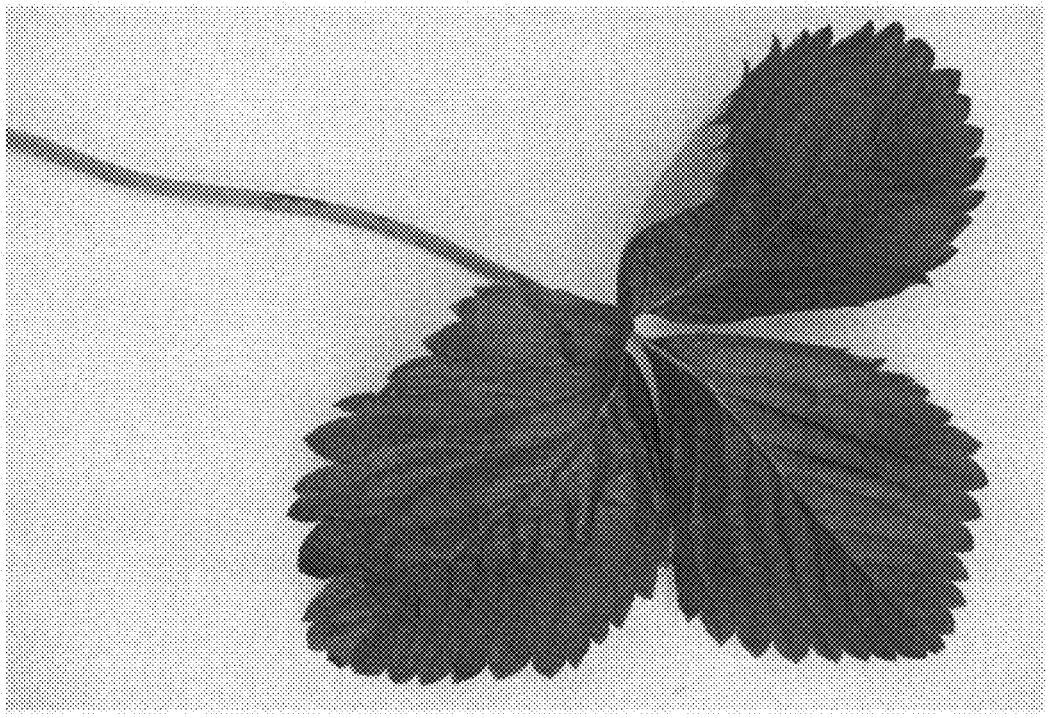
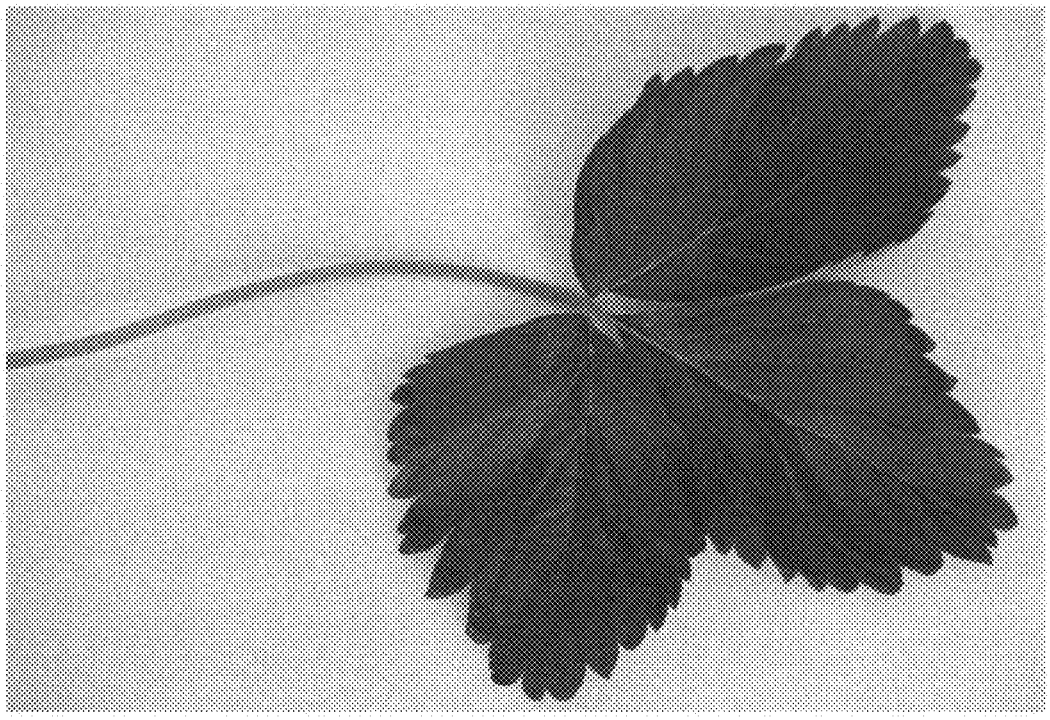

* * * * *